United States Patent
Eilat et al.

(10) Patent No.: US 10,987,306 B2
(45) Date of Patent: Apr. 27, 2021

(54) METHODS OF TREATMENT OF VAGINOSIS AND VULVOVAGINITIS

(71) Applicant: EVE Pharma Ltd., Or-Yehuda (IL)

(72) Inventors: Eran Eilat, Herzliya (IL); Stephen Cherkez, Caesarea (IL)

(73) Assignee: Eve Pharma Ltd., Or-Yehuda (IL)

( * ) Notice: Subject to any disclaimer, the term of this patent is extended or adjusted under 35 U.S.C. 154(b) by 0 days.

(21) Appl. No.: 15/812,457

(22) Filed: Nov. 14, 2017

(65) Prior Publication Data
US 2018/0064647 A1 Mar. 8, 2018

Related U.S. Application Data

(63) Continuation of application No. PCT/IB2016/000808, filed on May 26, 2016.

(60) Provisional application No. 62/168,031, filed on May 29, 2015.

(51) Int. Cl.
| | |
|---|---|
| *A61K 31/4196* | (2006.01) |
| *A61K 31/4164* | (2006.01) |
| *A61P 15/02* | (2006.01) |
| *A61K 9/06* | (2006.01) |
| *A61K 9/00* | (2006.01) |
| *A61K 9/127* | (2006.01) |
| *A61K 9/20* | (2006.01) |
| *A61K 9/48* | (2006.01) |

(52) U.S. Cl.
CPC ............. *A61K 9/06* (2013.01); *A61K 9/0034* (2013.01); *A61K 9/0036* (2013.01); *A61K 9/1278* (2013.01); *A61K 9/2081* (2013.01); *A61K 9/4891* (2013.01)

(58) Field of Classification Search
CPC .............. A61K 31/4196; A61K 31/4164
USPC .......................... 514/383, 396, 397
See application file for complete search history.

(56) References Cited

U.S. PATENT DOCUMENTS

| | | | |
|---|---|---|---|
| 5,269,321 A | 12/1993 | MacDonald et al. | |
| 5,769,813 A | 6/1998 | Peiler et al. | |
| 6,899,890 B2 | 5/2005 | Kirschner et al. | |
| 8,747,870 B2 | 6/2014 | Gupta et al. | |
| 2003/0017207 A1* | 1/2003 | Lin ..................... A61K 9/0034 | 424/486 |
| 2003/0180366 A1 | 9/2003 | Kirschner et al. | |
| 2010/0285094 A1 | 11/2010 | Gupta | |
| 2011/0158920 A1 | 6/2011 | Morley et al. | |
| 2012/0003685 A1 | 5/2012 | Kritzman et al. | |
| 2013/0129797 A1 | 5/2013 | Gupta et al. | |
| 2015/0320675 A1 | 11/2015 | Kiser et al. | |

FOREIGN PATENT DOCUMENTS

| | | |
|---|---|---|
| RU | 2320322 C2 | 3/2008 |
| WO | 2007/124132 A2 | 11/2007 |
| WO | 2008155589 A2 | 12/2008 |
| WO | 2009081097 A1 | 7/2009 |
| WO | 2014/113693 A1 | 7/2014 |

OTHER PUBLICATIONS

Hiorth et al., Pharmaceutics, 2014, vol. 6, pp. 494-511 (Year: 2014).*
Degim et al., Drug Delivery, 2008, vol. 15, No. 4, pp. 259-265 (Year: 2008).*
Lalan et al., "Applications of polymers in vaginal drug delivery", Chapter 10, pp. 351-378, Applications of Polymers in Drug Delivery, Jan. 2014 (Year: 2014).*
International Search Report and Written Opinion from International Application No. PCT/IB2016/000808 dated Oct. 21, 2016.
CERVIDIL®, Brand of dinoprostone vaginal insert, Rev. 04/10, RMC 226, Controlled Therapeutics, Forest Pharmaceuticals, Inc.
European Search Report to corresponding EP Application No. 16802640.9 completed Nov. 23, 2018 (8 pages).
Balamuralidhara et al., "pH Sensitive Drug Delivery Systems: A Review", American Journal of Drug Discovery and Development, 1, (1): 24-28, 2011.

\* cited by examiner

*Primary Examiner* — Raymond J Henley, III
(74) *Attorney, Agent, or Firm* — Greenberg Traurig LLP

(57) ABSTRACT

The present invention provides a pH dependent vaginal composition delivering a therapeutically effective amount of at least one active essentially at a pH above 4.5. The composition provides a diagnostic visual pH indication of the presence of vulvovaginitis at pH above 4.5. In the absence of such indication, the treatment may be discontinued. Another visual signal is the retrieval of the unchanged composition, which also points to a normal pH at or below 4.5 and absence of vulvovaginitis.

19 Claims, No Drawings

METHODS OF TREATMENT OF VAGINOSIS AND VULVOVAGINITIS

CROSS REFERENCE TO RELATED APPLICATIONS

This application is a continuation of International Application No. PCT/IB2016/000808, filed May 26, 2016, which claims priority to and the benefit of U.S. Provisional Patent Application Ser. No. 62/168,031, filed on May 29, 2015, the entire contents of each of which are hereby incorporated by reference in its entirety.

FIELD OF THE INVENTION

The present invention relates to topical compositions and methods of treatment of vaginal disorders.

BACKGROUND

Vaginal disorders are widespread and include a number of different conditions, of which the most common, are vaginal infections, such as, for example, vulvovaginitis, caused by bacterial vaginosis (such as trichomoniasis), yeast infection (such as candida), atrophic vaginitis, but also other causative factors such as viruses, parasites, environmental factors, allergens, sexually transmitted infections, chemicals (soap, bath oils, spermicidal jelly) and menopause. Currently, there are a number of oral and topically (vaginal) applied formulations for the treatment of vaginal conditions, including creams, gels, jellies, troches, suppositories.

The symptoms of vulvovaginitis include irritation of the genital area, genital itching, vaginal discharge, discomfort, pain and foul odor.

The vaginal discharge in bacterial vaginosis is thin and milky with a strong fishy odor. This condition is due to a change in the balance of bacteria normally present in the vagina.

Vulvovaginitis may be diagnosed, and medication prescribed during a physician's office visit. One of the signs of vulvovaginitis is a change from the normal vaginal pH, which is around 4.5. A pH reading to a level higher than 4.5 is an important tool in the diagnosis of vulvovaginitis.

Many women suffer from chronic recurring vulvovaginitis and are treated with medication available over-the-counter (OTC) without a first diagnosis or without repeating the diagnosis stage. This opens an avenue to futile use of medication by the female patient at the first sign of vaginal discomfort. Repeated futile use of medication may give rise to bacterial resistance to medication, and this should be avoided, hence reduction of antibiotic use is a long felt need.

SUMMARY

In one embodiment, the present invention provides a pH dependent vaginal composition delivering a therapeutically effective amount of at least one active essentially at a pH above 4.5.

In one embodiment, the pH-dependent vaginal composition is in a form selected from the group consisting of a pH-dependent vaginal capsule, a pH-dependent vaginal insert, a pH-dependent suppository, a pH-dependent cream, a pH-dependent gel, a pH-dependent foam, and a pH-dependent suspension.

In one embodiment, the at least one active is selected from the group consisting of butoconazole, clotrimazole, miconazole, terconazole, tioconazole, clindamycin, fluconazole, metronidazole, nystatin, estrogens, progestogens, and combinations thereof.

In one embodiment, the pH-dependent vaginal capsule further comprises a capsule wall configured to disintegrate at pH values greater than pH 4.5, wherein the disintegration is configured to deliver the at least one active.

In one embodiment, the pH-dependent vaginal capsule is filled with a sustained release composition, containing at least one active.

In one embodiment, the pH-dependent vaginal capsule further comprises a coating configured to disintegrate at pH values greater than pH 4.5, wherein the disintegration is configured to deliver the at least one active.

In one embodiment, the pH-dependent vaginal insert further comprises a pH-dependent polymer formulated as a matrix configured to deliver the at least one active at pH values greater than pH 4.5.

In one embodiment, the polymer is a hydrogel.

In one embodiment, the polymer is configured to deliver the at least one active in a sustained release manner.

In one embodiment, the polymer is configured to deliver the at least one active in a controlled-release manner.

In one embodiment, the pH-dependent suppository further comprises a coating configured to disintegrate at pH values greater than pH 4.5, wherein the disintegration is configured to deliver the at least one active.

In one embodiment, the pH dependent cream is formulated in a liposome configured to encapsulate the at least one active, and deliver the at least one active at pH values greater than pH 4.5.

In one embodiment, the pH dependent gel is formulated in a liposome configured to encapsulate the at least one active, and deliver the at least one active at pH values greater than pH 4.5.

In one embodiment, the pH dependent foam is formulated in a liposome configured to encapsulate the at least one active, and deliver the at least one active at pH values greater than pH 4.5.

In one embodiment, the pH dependent suspension is formulated in a liposome configured to encapsulate the at least one active, and deliver the at least one active at pH values greater than pH 4.5.

In one embodiment, the present invention provides a method of treating a vaginal disorder in a subject in need thereof, comprising administering a therapeutically effective amount of the pH-dependent vaginal composition according to an embodiment of the present invention to the subject one to three times per day, for one to seven days.

In one embodiment, the pH dependent vaginal composition is contained in a pouch configured to retrieve the composition, wherein the pouch comprises a tape configured to retrieve the pouch.

In one embodiment, the tape is impregnated with a pH indicator configured to provide a visual indication of the vaginal pH, wherein the visual indication is indicative of the presence of vulvovaginitis or normal vaginal pH, for diagnostic purposes.

In one embodiment, the visual indication of normal vaginal pH is a signal to discontinue therapy.

DETAILED DESCRIPTION

For clarity of disclosure, and not by way of limitation, the detailed description of the invention is divided into the following subsections that describe or illustrate certain features, embodiments or applications of the present invention.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "effective amount" or "therapeutically effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Topical vaginal compositions and methods of treatment of vaginal disorders are disclosed herein.

The compositions according to some embodiments of the instant invention provide methods of treatment which provide medication to the vagina only when really needed.

According to aspects illustrated herein, there are provided topical vaginal compositions in the form of vaginal capsules, vaginal inserts, vaginal suppositories, creams, gels, foams or suspensions.

The active pharmaceutical ingredients (APIs or actives in short) in the compositions of the instant invention are delivered essentially at pH values above 4.5. Thus, without intending to be limited to any particular theory, in the event the medication is inadvertently taken by a female patient whose vaginal pH is 4.5 or lower (normal pH), the API will not be delivered and the vaginal medication will be eliminated by the body as such or removed using an integral retrieval system.

In addition, the compositions of the instant invention may optionally be devised for sustained release delivery of the actives, thus enabling to be used only once instead of several days in a row, or once daily instead of several times per day.

In some embodiments, the present invention provides a pH dependent vaginal composition delivering a therapeutically effective amount of at least one active essentially at a pH above 4.5.

In some embodiments, the pH-dependent vaginal composition is in a form selected from the group consisting of a pH-dependent vaginal capsule, a pH-dependent vaginal insert, a pH-dependent suppository, a pH-dependent cream, a pH-dependent gel, a pH-dependent foam, and a pH-dependent suspension.

In some embodiments, the at least one active is selected from the group consisting of butoconazole, clotrimazole, miconazole, terconazole, tioconazole, clindamycin, fluconazole, metronidazole, nystatin, estrogens, progestogens, and combinations thereof.

In some embodiments, the pH-dependent vaginal capsule further comprises a capsule wall configured to disintegrate at pH values greater than pH 4.5, wherein the disintegration is configured to deliver the at least one active.

In some embodiments, the capsule wall configured to disintegrate at pH values greater than pH 4.5 is water insoluble at a pH of 4.5 and below. In some embodiments, the capsule wall configured to disintegrate at pH values greater than pH 4.5 is water soluble at a pH of greater than 4.5. In some embodiments, the capsule wall configured to disintegrate at pH values greater than pH 4.5 is water soluble at a pH of greater than 5. In some embodiments, the capsule wall configured to disintegrate at pH values greater than pH 4.5 is water soluble at a pH of greater than 5.5. In some embodiments, the capsule wall configured to disintegrate at pH values greater than pH 4.5 is water soluble at a pH of greater than 6. In some embodiments, the capsule wall configured to disintegrate at pH values greater than pH 4.5 is water soluble at a pH of greater than 6.5. In some embodiments, the capsule wall configured to disintegrate at pH values greater than pH 4.5 is water soluble at a pH of greater than 7. In some embodiments, the capsule wall configured to disintegrate at pH values greater than pH 4.5 is water soluble at a pH of greater than 7.5. In some embodiments, the capsule wall configured to disintegrate at pH values greater than pH 4.5 is water soluble at a pH of greater than 8.5.

In some embodiments, the pH-dependent vaginal capsule is filled with a sustained release composition, containing at least one active.

In some embodiments, the pH-dependent vaginal capsule further comprises a coating configured to disintegrate at pH values greater than pH 4.5, wherein the disintegration is configured to deliver the at least one active.

In some embodiments, the coating configured to disintegrate at pH values greater than pH 4.5 is water insoluble at a pH of 4.5 and below. In some embodiments, the coating configured to disintegrate at pH values greater than pH 4.5 is water soluble at a pH of greater than 4.5. In some embodiments, the coating configured to disintegrate at pH values greater than pH 4.5 is water soluble at a pH of greater than 5. In some embodiments, the coating configured to disintegrate at pH values greater than pH 4.5 is water soluble at a pH of greater than 5.5. In some embodiments, the coating configured to disintegrate at pH values greater than pH 4.5 is water soluble at a pH of greater than 6. In some embodiments, the coating configured to disintegrate at pH values greater than pH 4.5 is water soluble at a pH of greater than 6.5. In some embodiments, the coating configured to disintegrate at pH values greater than pH 4.5 is water soluble at a pH of greater than 7. In some embodiments, the coating configured to disintegrate at pH values greater than pH 4.5 is water soluble at a pH of greater than 7.5. In some embodiments, the coating configured to disintegrate at pH values greater than pH 4.5 is water soluble at a pH of greater than 8.5.

In some embodiments, the pH-dependent vaginal insert further comprises a pH-dependent polymer formulated as a matrix configured to deliver the at least one active at pH values greater than pH 4.5.

In some embodiments, the polymer is a hydrogel.

In some embodiments, the polymer is configured to deliver the at least one active in a sustained release manner.

In some embodiments, the polymer is configured to deliver the at least one active in a controlled-release manner.

In various aspects of the present invention, the polymer is configured to release the at least one active in vivo and/or in the presence of a change in pH for at least 10 minutes. In a further aspect, release of the at least one active continues for at least 30 minutes. In a still further aspect, release of the at least one active agent continues for at least 1 hour. In yet a further aspect, release of the polymer and/or active agent continues for at least 5 hours. In an even further aspect, release of the at least one active agent continues for at least 10 hours. In a still further aspect, release of the at least one active agent continues for at least 12 hours. In yet a further aspect, release of the at least one active agent continues for at least 24 hours. In an even further aspect, release of the at least one active agent continues for at least 2 days. In a still further aspect, release of the at least one active agent continues for at least 3 days. In yet a further aspect, release of the at least one active agent continues for at least 4 days. In an even further aspect, release of the at least one active agent continues for at least 5 days. In a still further aspect, release of the at least one active agent continues for at least 6 days. In yet a further aspect, release of the at least one active agent continues for at least 7 days.

In various aspects, the controlled-release device exhibits release rates of from about 0.001 mg of at least one active agent per day to about 10 mg of at least one active agent per day. In a further aspect, controlled-release device exhibits release rates of from about 0.001 mg to about 10 mg, from about 0.005 mg to about 10 mg, from about 0.01 mg to about 10 mg, from about 0.025 mg to about 10, from about 0.05 mg to about 10 mg, from about 0.075 mg to about 10 mg, from about 0.1 mg to about 10 mg, from about 0.15 mg to about 10 mg, from about 0.2 mg to about 10 mg, from about 0.5 mg to about 10 mg, from about 0.75 mg to about 10 mg, from about 1 mg to about 10 mg, from about 2 mg to about 10, from about 3 mg to about 10, from about 4 mg to about 10 mg, from about 5 mg to about 10 mg, from about 0.001 mg to about 5 mg, from about 0.001 mg to about 4 mg, from about 0.001 mg to about 3 mg, from about 0.001 mg to about 2 mg, from about 0.001 mg to about 1 mg, from about 0.001 mg to about 0.75 mg, from about 0.001 mg, to about 0.5 mg, from about 0.001 mg to about 0.2 mg, from about 0.001 mg to about 0.015 mg, from about 0.001 mg to about 20 mg, from about 0.001 mg to about 0.075 mg, from about 0.001 mg to about 0.05 mg, from about 0.001 mg to about 0.025 mg, from about 0.001 mg to about 0.01 mg, or from about 0.001 mg to about 0.005 mg.

In some embodiments, the pH-dependent suppository further comprises a coating configured to disintegrate at pH values greater than pH 4.5, wherein the disintegration is configured to deliver the at least one active.

In some embodiments, the pH dependent cream is encapsulated in a liposome configured to encapsulate the at least one active, and deliver the at least one active at pH values greater than pH 4.5.

In some embodiments, the pH dependent gel is encapsulated in a liposome configured to encapsulate the at least one active, and deliver the at least one active at pH values greater than pH 4.5.

In some embodiments, the pH dependent foam is encapsulated in a liposome configured to encapsulate the at least one active, and deliver the at least one active at pH values greater than pH 4.5.

In some embodiments, the pH dependent suspension is encapsulated in a liposome configured to encapsulate the at least one active, and deliver the at least one active at pH values greater than pH 4.5.

While the compositions of the instant invention come in different forms (vaginal capsules, vaginal inserts, vaginal suppositories, creams, gels, foams or suspensions), they share a common characteristic: the delivery of the APIs is pH-dependent, in such a way that they are delivered essentially at pH values above 4.5. At pH values at or below 4.5, the compositions are eliminated or removed from the vagina, essentially unchanged.

The pH-dependent delivery is achieved in various ways, depending on the type of the composition:

pH-Dependent Vaginal Capsules:

In some embodiments, the pH-dependent delivery of the APIs from the vaginal capsules is achieved either by selecting a pH-dependent capsule wall (such as pH-dependent softgel capsules) or by coating the capsule with a pH-dependent coating, both designed to deliver the APIs essentially at pH above 4.5.

The optional sustained-release delivery is obtained by filling the capsule with a sustained-release composition containing the API.

pH-Dependent Vaginal Inserts:

In some embodiments, the pH-dependent API delivery is obtained by using a pH-dependent polymer (such as a hydrogel) insert in the form of a vaginal insert. In some embodiments, the insert is formulated as a matrix composition, optionally as a controlled-release or delayed-release composition.

In some embodiments, the vaginal insert is optionally contained in a pouch of knitted retrieval system including a long tape used for retrieval of the remaining insert after delivery of the active. The API delivery takes place essentially at pH above 4.5. In the event the pH is at or below 4.5, the insert will be retrieved or eliminated essentially unchanged.

Optionally, the above long tape of the retrieval system may be impregnated with a pH indicator. About 0.5-12 hrs. after the insertion, the patient may remove the long tape, whose color will provide a visual indication of the vaginal pH, indicative of the presence of vulvovaginitis. In the event the pH is at or below 4.5 (normal vaginal pH), the patient may discard the insert and discontinue treatment.

pH-Dependent Cream:

In some embodiments, the pH-dependent delivery of the API from the cream is obtained by formulating the cream composition in such a way that the API is encapsulated in a pH-dependent liposome, delivering the API essentially at pH values above 4.5.

pH-Dependent Gels:

Similarly, gels comprising the API encapsulated in pH-dependent liposomes are prepared.

pH-Dependent Foams:

In some embodiments, the API is encapsulated in a pH-dependent liposome.

pH-Dependent Suspensions:

In some embodiments, the API is encapsulated in a pH-dependent suspension.

pH-Dependent Suppositories:

In some embodiments, the pH-dependent release of the API in this case is achieved by using a vaginal suppository encapsulated in a pH-dependent coating.

Methods of Treatment

In some embodiments, the present invention provides a method of treating a vaginal disorder in a subject in need thereof, comprising administering a therapeutically effective amount of the pH-dependent vaginal composition according to an embodiment of the present invention to the subject one to three times per day, for one to seven days.

In some embodiments, the vaginal disorder is selected from the group consisting of: vulvovaginitis, a bacterial infection, trichomoniasis, thrush, bacterial vaginosis, vaginal candidiasis, vulvar candidiasis, and vaginal itching.

In some embodiments, the pH dependent vaginal composition is contained in a pouch configured to retrieve the composition, wherein the pouch comprises a tape configured to retrieve the pouch.

In some embodiments, the tape is impregnated with a pH indicator configured to provide a visual indication of the vaginal pH, wherein the visual indication is indicative of the presence of vulvovaginitis and normal vaginal pH.

In some embodiments, the visual indication of normal vaginal pH is a signal to discontinue therapy.

In some embodiments, the visual indication of normal vaginal pH at or below 4.5 is a signal to discontinue therapy.

In some embodiments, the visual indication of a composition eliminated or retrieved unchanged form the vagina is a signal to discontinue therapy.

In some embodiments, the visual indication prevents unnecessary use of the pH-dependent vaginal composition according to some embodiments of the present invention.

In another embodiment, there is provided a method of treatment of a vaginal disorder in a patient in need thereof, wherein administrating a therapeutically effective dose of at least one API selected from the group consisting of: butoconazole, clotrimazole, miconazole, terconazole, tioconazole, clindamycin, fluconazole, metronidazole, nystatin, estrogens, progestogens and combinations thereof, formulated in one of the compositions of the instant invention, in the form of vaginal capsule, vaginal insert, vaginal suppository, cream, gel, foam or suspension once to three times daily for 1-7 days.

In an embodiment, there is provided a pouch of knitted retrieval system including a long tape used for retrieval of the remaining insert after delivery of the active, wherein the long tape is pH sensitive and changes its color as results of higher pH level, which is indicative of the presence of vulvovaginitis.

In another embodiment, there is provided a pH-dependent vaginal suppository wherein a vaginal suppository is coated with a pH-dependent coating, delivering the API essentially at pH values above 4.5.

In some embodiments, the at least one active agent is administered in a therapeutically effective amount. In a still further aspect, the therapeutically effective amount is from about 0.01 wt % to about 50 wt %. In yet a further aspect, the therapeutically effective amount is from about 0.01 wt % to about 40 wt %. In an even further aspect, the therapeutically effective amount is from about 0.01 wt % to about 30 wt %. In a still further aspect, the therapeutically effective amount is from about 0.01 wt % to about 20 wt %. In yet a further aspect, the therapeutically effective amount is from about 0.01 wt % to about 10 wt %. In an even further aspect, the therapeutically effective amount is from about 1 wt % to about 50 wt %. In a still further aspect, the therapeutically effective amount is from about 5 wt % to about 50 wt %. In yet a further aspect, the therapeutically effective amount is from about 10 wt % to about 50 wt %. In an even further aspect, the therapeutically effective amount is from about 20 wt % to about 50 wt %. In a still further aspect, the therapeutically effective amount is from about 30 wt % to about 50 wt %. In yet a further aspect, the therapeutically effective amount is from about 40 wt % to about 50 wt %.

In some embodiments, the at least one active agent is contained within a dosage form selected from the group comprising a pH-dependent vaginal capsule, a pH-dependent vaginal insert, a pH-dependent suppository, a pH-dependent cream, a pH-dependent gel, a pH-dependent foam, or a pH-dependent suspension. In these embodiments, the therapeutically effective amount of the at least one active agent is from about 1 mg to about 1,000 mg per dosage form. In a still further aspect, the therapeutically effective amount is from about 1 mg to about 750 mg per dosage form. In yet a further aspect, the therapeutically effective amount is from about 1 mg to about 500 mg per dosage form. In an even further aspect, the therapeutically effective amount is from about 1 mg to about 250 mg per dosage form. In a still further aspect, the therapeutically effective amount is from about 1 mg to about 50 mg per dosage form. In yet a further aspect, the therapeutically effective amount is from about 50 mg to about 1,000 mg per dosage form. In an even further aspect, the therapeutically effective amount is from about 250 mg to about 1,000 mg per dosage form. In a still further aspect, the therapeutically effective amount is from about 500 mg to about 1,000 mg per dosage form. In yet a further aspect, the therapeutically effective amount is from about 750 mg to about 1,000 mg per dosage form.

In some embodiments, the therapeutically effective amount is a dosage form comprising from about 1 wt % to about 2.0 wt % of active. In some embodiments, the therapeutically effective amount is a dosage comprising from about 1.1 wt % of the at least one active. In some embodiments, the therapeutically effective amount is a dosage comprising from about 1.2 wt % of the at least one active. In some embodiments, the therapeutically effective amount is a dosage comprising about 1.3 wt % of the at least one active.

In some embodiments, the active is metronidazole and the therapeutically effective amount is a dosage form comprising from about 1 wt % to about 2.0 wt % of metronidazole, particularly 1.3%. In some embodiments, the therapeutically effective amount is a dosage comprising from about 1.1 wt % of the at least one active. In some embodiments, the therapeutically effective amount is a dosage comprising from about 1.2 wt % of the at least one active. In some embodiments, the therapeutically effective amount is a dosage comprising about 1.3 wt % of metronidazole.

In some embodiments, 0.5 g of the dosage form is administered. In some embodiments, 1 g of the dosage form is administered. In some embodiments, 1.5 g of the dosage form is administered. In some embodiments, 2 g of the dosage form is administered. In some embodiments, 2.5 g of the dosage form is administered. In some embodiments, 3 g of the dosage form is administered. In some embodiments, 3.5 g of the dosage form is administered. In some embodiments, 4 g of the dosage form is administered. In some embodiments, 4.5 g of the dosage form is administered. In some embodiments, 5 g of the dosage form is administered.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method of treatment of vaginosis or vulvovaginitis comprising:
administering to a subject in need thereof a vaginal solid composition comprising a therapeutically effective amount of at least one active agent, a pH-dependent polymer, and optionally a pH indicator, wherein the pH-dependent polymer dissolves at a pH greater than 4.5, wherein the subject in need thereof has a vaginal pH greater than 4.5, wherein the vaginal pH greater than 4.5 is indicative of vaginosis and vulvovaginitis, wherein the solid composition is a capsule, an insert, a matrix or suppository,
retrieving the composition,
discontinuing treatment of vaginosis or vulvovaginitis if the solid composition is not disintegrated, if the optional pH indicator indicates a pH of 4.5 or below, or combination thereof.

2. The method of treatment of claim 1, wherein the at least one active agent is selected from the group consisting of butoconazole, clotrimazole, miconazole, terconazole, tioconazole, clindamycin, fluconazole, metronidazole, nystatin, estrogens, progestogens, and combinations thereof.

3. The method of treatment of claim 1, wherein the at least one active agent is metronidazole.

4. The method of treatment of claim 1, comprising administering a therapeutically effective amount of the composition to the subject one to three times per day, for one to seven days.

5. The method of treatment of claim 1, wherein the composition is a capsule and wherein the capsule wall is configured to disintegrate at pH values greater than pH 4.5 and is water insoluble at a pH of 4.5 and below.

6. The method of treatment of claim 1, wherein the composition is a capsule comprising a pH-dependent polymer coating and, wherein upon administration of the composition, the pH-dependent polymer coating disintegrates at pH values greater than 4.5 to deliver the at least one active agent.

7. The method of treatment of claim 1, wherein the composition is configured to deliver the at least one active in a sustained release manner.

8. The method of treatment of claim 1, wherein the vaginal composition is formulated as a matrix comprising a pH-dependent polymer configured to deliver the at least one active agent at pH values greater than 4.5.

9. The method of treatment of claim 6, wherein the pH-dependent polymer coating is water insoluble at a pH of 4.5 and below, and is water soluble at a pH greater than 4.5.

10. The method of treatment of claim 6, wherein the pH-dependent polymer coating is water soluble at a pH greater than 5.

11. The method of treatment of claim 6, wherein the pH-dependent polymer coating is water soluble at a pH greater than 5.5.

12. The method of treatment of claim 6, wherein the pH-dependent polymer coating is water soluble at a pH greater than 6.

13. The method of treatment of claim 1, wherein the composition is contained in a pouch configured to retrieve the composition, wherein the pouch comprises a tape configured to retrieve the pouch.

14. The method of treatment of claim 13, wherein the tape is impregnated with a pH indicator to provide a visual indication of the vaginal pH, wherein the visual indication is indicative of the presence of vaginosis and vulvovaginitis at pH above 4.5 or of a normal vaginal pH at or below 4.5.

15. A method of treatment of vaginosis or vulvovaginitis comprising:
administering to a subject in need thereof a solid vaginal composition comprising a therapeutically effective amount of at least one active agent and a pH-dependent polymer coating, wherein the active agent is delivered at pH greater than 4.5, wherein the pH-dependent polymer coating is configured to disintegrate at pH values greater than pH 4.5, wherein the pH-dependent polymer coating is water insoluble at a pH of 4.5 and below, and is water soluble at a pH greater than 4.5, wherein the subject in need thereof has a vaginal pH greater than 4.5, wherein the vaginal pH greater than 4.5 is indicative of vaginosis and vulvovaginitis, wherein the solid composition is a capsule, a matrix, or a suppository, retrieving the composition, discontinuing treatment of vaginosis or vulvovaginitis if the solid composition is not disintegrated.

16. The method of claim 1, wherein the pH-dependent polymer is coated on the suppository, wherein the coating is configured to deliver the at least one active at pH values greater than 4.5.

17. The method of claim 1 comprising retrieving the composition after 0.5 to 12 hours.

18. A method to deliver vaginally at least one active agent at a vaginal pH greater than 4.5, the method comprising:

administering to a subject in need thereof a solid vaginal composition to treat vaginosis or vulvovaginitis, the solid vaginal composition comprising a therapeutically effective amount of the at least one active agent and a coat comprising a pH-dependent polymer, wherein the pH-dependent polymer coating is water insoluble at a pH of 4.5 and below, and is water soluble at a pH greater than 4.5, retrieving the composition, discontinuing treatment of vaginosis or vulvovaginitis if the composition is not disintegrated.

19. The method of claim 18, wherein the solid vaginal composition is a suppository.

* * * * *